US007659256B2

(12) United States Patent
Najarian

(10) Patent No.: US 7,659,256 B2
(45) Date of Patent: *Feb. 9, 2010

(54) COMBINATION THERAPY FOR EFFECTING WEIGHT LOSS AND TREATING OBESITY

(75) Inventor: Thomas Najarian, Los Osos, CA (US)

(73) Assignee: Vivus, Inc., Mountain View, CA (US)

( * ) Notice: Subject to any disclaimer, the term of this patent is extended or adjusted under 35 U.S.C. 154(b) by 583 days.

This patent is subject to a terminal disclaimer.

(21) Appl. No.: 11/385,199

(22) Filed: Mar. 20, 2006

(65) Prior Publication Data

US 2006/0234951 A1 Oct. 19, 2006

Related U.S. Application Data

(63) Continuation-in-part of application No. 10/454,368, filed on Jun. 3, 2003, now Pat. No. 7,056,890, which is a continuation-in-part of application No. 09/593,555, filed on Jun. 14, 2000, now abandoned.

(60) Provisional application No. 60/181,265, filed on Feb. 9, 2000, provisional application No. 60/178,563, filed on Jan. 26, 2000, provisional application No. 60/139,022, filed on Jun. 14, 1999.

(51) Int. Cl.
*A61K 31/135* (2006.01)
*A61K 31/70* (2006.01)

(52) U.S. Cl. .......................................... 514/23; 514/646

(58) Field of Classification Search ....................... None
See application file for complete search history.

(56) References Cited

U.S. PATENT DOCUMENTS

| | | | |
|---|---|---|---|
| 4,513,006 A | 4/1985 | Maryanoff et al. | |
| 4,792,569 A | 12/1988 | Maryanoff et al. | |
| 4,895,845 A | 1/1990 | Seed | |
| 5,242,942 A | 9/1993 | Costanzo et al. | |
| 5,266,591 A | 11/1993 | Wierzbicki | |
| 5,273,993 A | 12/1993 | Lo et al. | |
| 5,498,629 A | 3/1996 | Costanzo et al. | |
| 5,527,788 A * | 6/1996 | Svec et al. | 514/169 |
| 5,543,405 A | 8/1996 | Keown et al. | |
| 5,753,693 A | 5/1998 | Shank | |
| 5,753,694 A | 5/1998 | Shank | |
| 5,795,895 A | 8/1998 | Anchors | |
| 5,900,418 A | 5/1999 | Viner | |
| 6,071,537 A | 6/2000 | Shank | |
| 6,201,010 B1 | 3/2001 | Cottrell | |
| 6,323,236 B2 | 11/2001 | McElroy | |
| 6,362,220 B1 | 3/2002 | Cottrell | |
| 2004/0002462 A1 | 1/2004 | Najarian | |

FOREIGN PATENT DOCUMENTS

WO WO 00/50020 8/2000

WO WO 00/76493 12/2000

OTHER PUBLICATIONS

Alger, S. et al "Effect of phenylpropanolamine on energy expenditure . . . " Am. J. Clin. (1993) vol. 57, pp. 120-126.*
Pi-Sunyer, F. "A review of long-term studies evaluating the efficacy of weight loss . . . " Clin. Ther. (1996) vol. 18, No. 6, pp. 1006-1035.*
Physicians' Desk Reference (1999) entry for phentermine.*
Bray et al. (1999), "Current and Potential Drugs for Treatment of Obesity", Endocrine Reviews 20(6):805-875.
Merck Index, The, an Encyclopedia of Chemicals, Drugs, and Biologicals, Twelfth Edition, Published by Merck Research Laboratories, 1996.
Privitera, (1997), "Topiramate: A New Antiepileptic Drug", The Annals of Pharmacotherapy, vol. 31, pp. 1164-1173.
Shapira, (2000), "Treatment of Binge-Eating Disorder With Topiramate: A Clinical Case Series", J. Clin. Psychiatry, 61:5, pp. 368-372.
U.S. Appl. No. 60/139,022, Issue Date Dec. 21, 2000, Najarian, filed Jun. 14, 1999.
U.S. Appl. No. 60/178,563, Issue Date Dec. 21, 2000, Najarian, filed Jan. 26, 2000.
U.S. Appl. No. 60/181,265, Issue Date Dec. 21, 2000, Najarian, filed Feb. 9, 2000.
*Physician's Desk Reference*, 49$^{th}$ Edition, pp. 2508-2509 (1995).
Bradley et al. (1999), "Bupropion SR with Phentermine for Weight Reduction," *Book of Abstracts, American Psychiactric Association Meeting* (distributed to meeting attendees), Washington, D.C. (abstract only).
Bray et al. (2002), "Topiramate Produces Dose-Related Weight Loss," 62$^{nd}$ *Annual American Diabetes Association Meeting*, San Francisco.
Carek, et al., (1999) "Current concepts in the pharmacological management of obesity," *Drugs* 6:883-904.
Coyne (1997), letter regarding Ionamin to the U.S. Food and Drug Administration, printed from http://www.fda.gov/medwatch/safety/1997)/ionami2.htm.
FDC Reports, Inc. (1999), "Appetite Suppression Drugs Excluded by 81 % of Employers—PBMI Survey," *The Green Sheet* 48(19):3.
Gadde et al. (1999), "Bupropion SR in Obesity: A Randomized Double-Blind Placebo-Controlled Study," *Obesity Research* 7(Suppl. 1):51F, Abstract 0136; Annual Meeting of the North American Association for the Study of Obesity, Charlestown, S.C.
Griffen et al., (1998) "The 'phen-pro' diet drug combination," Arch. Intern. Med. 158:1278-1279.

(Continued)

*Primary Examiner*—Leigh C Maier
(74) *Attorney, Agent, or Firm*—Mintz Levin Cohn Ferris Glovsky & Popeo, P.C.

(57) ABSTRACT

The present invention features a novel therapy for effecting weight loss which involves treating a subject with a sympathomimetic agent (e.g., phentermine or a phentermine-like drug) in combination with an anticonvulsant sulfamate derivative (e.g., topiramate) such that the subject experiences weight loss.

The combination methods of the present invention also are effective against symptoms associated with Syndrome X. The invention also features pharmaceutical compositions and kits for use in the practice of these novel therapies.

29 Claims, No Drawings

OTHER PUBLICATIONS

Michelucci et al. (1998), "The Preclinical and Therapeutic Activity of the Novel Anticonvulsant Topiramate," *CNS Drug Reviews* 4(2):165-186.

Penovich et al. (1994), "Weight Loss in Patients Receiving Topiramate for Intractable Epilepsy," *Neurology* 44(Suppl. 2), Abstract 309P, 46th Annual Meeting of the American Academy of Neurology, Washington, D.C.

Potter et al. (1997), "Sustained Weight Loss Associated with 12-Month Topiramate Therapy," *Epilepsia* 38(Suppl. 8):97; Annual Meeting of the American Epilepsy Society, Boston, MA.

Raritan (2002), "Clinical Development of Topiramate for Obesity Extended to Simplify Dosing, Improve Tolerability," Johnson & Johnson Pharmaceutical Research & Development, LLC press release, printed from http://www.jnj.com/news finance/448.htm.

U.S. Food and Drug Administration (1997) "FASTIN (Phentermine HCl) Capsules," *Oct. 1997 Drug Labeling Changes*, printed from http://www.fea.gov/medwatch/safety/1997/oct97.htm.

U.S. Food and Drug Administration (1999), "IONAMIN (Phentermine Resin) Capsules," *Feb. 1998 Drug Labeling Changes*, printed from http://www.fea.gov/medwatch/safety/1998/feb99.htm.

Weintraub, et al., (1984) "A double-blind clinical trial in weight control," *Arch. Intern. Med*. 144:1143-1148.

Zarate (2000), "Antipsychotic Drug Side Effect Issues in Bipolar Manic Patients," *J. Clin Psychiatry* 61(Suppl. 8):52-61, Derwent.

\* cited by examiner

COMBINATION THERAPY FOR EFFECTING WEIGHT LOSS AND TREATING OBESITY

CROSS-REFERENCE TO RELATED APPLICATIONS

This application is a continuation-in-part of U.S. patent application Ser. No. 10/454,368, filed Jun. 3, 2003, which is a continuation-in-part of U.S. patent application Ser. No. 09/593,555, filed Jun. 14, 2000, now abandoned, which claims priority under 35 U.S.C. §119(e)(1) to provisional U.S. Patent Applications Ser. No. 60/139,022, filed Jun. 14, 1999, Ser. No. 60/178,563, filed Jan. 26, 2000, and Ser. No. 60/181,265, filed Feb. 9, 2000. The aforementioned patent applications are incorporated herein by reference in their entireties.

BACKGROUND OF THE INVENTION

About 97 million adults in the United States are overweight or obese. The medical problems caused by overweight and obesity can be serious and often life-threatening, and include diabetes, shortness of breath, gallbladder disease, hypertension, elevated blood cholesterol levels, cancer, arthritis, other orthopedic problems, reflux esophagitis (heartburn), snoring, sleep apnea, menstrual irregularities, infertility and heart trouble. Moreover, obesity and overweight substantially increase the risk of morbidity from hypertension, dyslipidemia, type 2 diabetes, coronary heart disease, stroke, gallbladder disease, osteoarthritis and endometrial, breast, prostate, and colon cancers. Higher body weights are also associated with increases in all-cause mortality. Most or all of these problems are relieved or improved by permanent significant weight loss. Longevity is likewise significantly increased by permanent significant weight loss.

Weight loss treatments vary depending, at least in part, on the degree of weight loss one is attempting to achieve in a subject as well as on the severity of overweight or obesity exhibited by the subject. For example, treatments such as low-fat diet and/or regular exercise are often adequate in cases where a subject is only mildly overweight. Such treatments can be enhanced by controlled use of over-the-counter appetite suppressants including caffeine, ephedrine and phenylpropanolamine (Acutrim®, Dexatrim®). Moreover, prescription medications including amphetamine, diethylpropion (Tenuate®), mazindol (Mazanor®, Sanorex®), phentermine (Fastin®, Ionamin®), phenmetrazine (Preludin®), phendimetrazine (Bontrol®, Plegine®, Adipost®, Dital®, Dyrexan®, Melfiat®, Prelu-2®, Rexigen Forte®), benzphetamine (Didrex®) and fluoxetine (Prozac®) are often used in the treatment of seriously overweight and/or obese subjects or patients. However, such treatments, at best, result in only ~5-10% weight loss (when accompanied with diet and exercise). Moreover, most of these treatments ultimately prove inadequate because they are either dangerous, ineffective or quickly lose their anorexient effect.

At least one class of these prescription medications, the phentermines (Fastin®, Ionamin®), have been used as monotherapy in the treatment of obesity for about 30 years. The phentermines are members of a class of drugs known as the sympathomimetics for their ability to mimic stimulation of the central nervous system. The phentermines act on the hypothalamus, an appetite control center of the brain. Phentermine monotherapy can increase weight loss when used in combination with diet and exercise, as compared to diet and exercise alone. However, the drug loses effectiveness after about two weeks and, in fact, is not approved by the FDA for use beyond six weeks. Moreover, weight loss may not be permanent, especially after the drug is discontinued. Phentermine treatment is also associated with side effects including nervousness, irritability, headache, sweating, dry-mouth, nausea, and constipation.

In general, available weight loss drugs have limited efficacy and some clinically significant side effects. Studies of the weight loss medications dexfenfluramine (Guy-Grand, B. et al. (1989) *Lancet* 2:1142-5), orlistat (Davidson, M. H. et al. (1999) *JAMA* 281:235-42), sibutramine (Bray, G. A. et al. (1999) *Obes. Res.* 7:189-98), and phentermine (Douglas, A. et al. (1983) *Int. J. Obes.* 7:591-5) have shown similar effectiveness. Studies for each demonstrated a weight loss of about 5% of body weight for drug compared with placebo. Other serious considerations limit the clinical use of these drugs. Dexfenfluramine was withdrawn from the market because of suspected heart valvulopathy, orlistat is limited by GI side effects, sibutramine can cause hypertension, and phentermine has limited efficacy.

Various combination therapies that include phentermine as one of the agents have been investigated and have met with mixed success. The phentermines were, up until around 1997, often prescribed along with fenfluramine (Pondimin®) or dexfenfluramine (Redux®), nicknamed "fen", as a combination therapy known as fen-phen. Fenfluramine is a potent releaser of serotonin from serotonergic neurons which acts on a cerebral appetite center. When combined with phentermine, fenfluramine had the effect of enhancing and extending the anorexient action of phentermine. However in 1997, the Food and Drug Administration ("FDA") asked manufacturers to withdraw Pondimin® and Redux® due to studies which strongly suggested that the drugs cause damage to the mitral valve of the heart and pulmonary hypertension.

More recently, it has been suggested that phentermine in combination with anti depressants is a potentially effective therapy for effecting weight loss, U.S. Pat. No. 5,795,895. In particular, the anti-depressants suggested for use in this new combination therapy are members of a class of compounds known as selective serotonin reuptake inhibitors (SSRIs) which include fluoxetine (Prozac®), sertraline (Zoloft®), fluvoxamine maleate (Luvox®) and trazodone hydrochloride (Desyrel®). The combination therapy is also suggested to treat coexisting depression and/or obsessive-compulsive disorder.

Phentermine has also recently been tested in combination with bupropion (Wellbutrin®) for the treatment of obesity. Bupropion is an antidepressant that inhibits dopamine reuptake, as compared to serotonin uptake. It is also used to treat Attention Deficit Disorder (ADHD), bipolar depression, chronic fatigue syndrome, cocaine addiction, nicotine addiction, and lower back pain. While bupropion alone had a modest effect as a weight loss agent (when prescribed to patients following a 1200 calorie per day diet), patients receiving phentermine in combination with bupropion experienced no greater weight loss than those receiving bupropion alone. Moreover, bupropion use has been associated with drug-induced seizures causing it to be removed from the market by the FDA for at least five years before its re-introduction in 1989.

Accordingly, there exists a need for new, more effective weight loss treatments which are accompanied by fewer adverse or undesirable side effects or less serious side effects. In particular, there exists a need for developing medical weight loss treatments which can potentially lower major endpoints such as death and/or myocardial infarction rates by directly treating obesity rather than treating the consequences of obesity (e.g., diabetes, hypertension, hyperlipidemia), as is currently the practice.

SUMMARY OF THE INVENTION

The present invention features a novel therapy for effecting weight loss which involves treating a subject with a sympathomimetic agent in combination with an anticonvulsant sulfamate derivative such that the subject experiences weight loss. In one aspect, the sympathomimetic agent is a compound having anorectic activity (e.g., amphetamine, methamphetamine, benzphetamine, phentermine, chlorphentermine, diethylpropran, phenmetrazine, and phendimetrazine). Preferably, the sympathomimetic agent is the drug phentermine (nicknamed "phen"). In another aspect, the anticonvulsant sulfamate derivative is the drug topiramate.

The combination methods of the present invention also are effective against symptoms associated with Syndrome X. Accordingly, in another aspect the invention features methods for treating Syndrome X with a combination of a sympathomimetic agent and an anticonvulsant sulfamate derivative (e.g., phentermine and topiramate, respectively) such that at least one symptom associated with Syndrome X is affected. Moreover, the combination methods of the present invention have been shown to have beneficial side effects, such as ameliorating sleep apnea and lowering blood pressure, blood glucose, blood lipid, and Hgb A1C levels. Accordingly, in another aspect the invention features methods for treating at least one side effect associated with obesity. In a preferred embodiment, at least one side effect of obesity is treated with a combination of a sympathomimetic agent in combination with an anticonvulsant sulfamate derivative.

The invention also features pharmaceutical compositions including therapeutically effective amounts of a sympathomimetic agent in combination with an anticonvulsant sulfamate derivative. Kits including the pharmaceutical compositions of the present invention are also featured (e.g., kits including the compositions packaged in a daily dosing regimen).

DETAILED DESCRIPTION OF THE INVENTION

The present invention is directed to a novel combination therapy for effecting weight loss in a subject. In particular, the present invention provides methods which involve treating the subject with a therapeutically effective amount of a combination of a sympathomimetic agent (e.g., phentermine or a phentermine-like compound) and an anticonvulsant sulfamate derivative (e.g., topiramate). The methods are particularly useful for the treatment of overweight and/or obesity, as well as in the treatment of Syndrome X.

The phrase "therapeutically effective amount" as used herein refers to the amount of an agent, compound, drug, composition, or combination of the invention which is effective for producing some desired therapeutic effect upon administration to a subject or patient (e.g., a human subject or patient). The phrase administering to a subject or administering to a patient refers to the process of introducing an agent, compound, drug, composition or combination of the invention into the subject or patient's body via an art-recognized means of introduction (e.g., orally, transdermally, via injection, etc.).

The term sympathomimetic agent is a term of art and refers to agents or compounds which "mimic" or alter stimulation of the sympathetic nervous system (e.g., stimulates the peripheral nervous system) of an organism (e.g., mimic the stimulation naturally effected by physical activity, psychological stress, generalized allergic reaction and other situations in which the organism is provoked).

Preferred sympathomimetic agents for use in the present invention as well as there general clinical uses or effects are set forth in Table 1.

TABLE I

Sympathomimetic Agents and Clinical Uses Thereof

General structure:

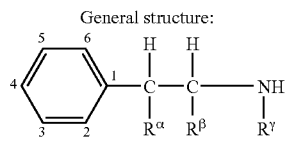

| Agent name | Ring substituent(s) | $R^\alpha$ | $R^\beta$ | $R^\gamma$ | α Receptor A N P V | β Receptor B C | CNS, 0 |
|---|---|---|---|---|---|---|---|
| Phenylethylamine | | H | H | H | | | |
| Epinephrine | 3-OH, 4-OH | OH | H | $CH_3$ | A, P, V | B, C | |
| Norepinephrine | 3-OH, 4-OH | OH | H | H | P | | |
| Epinine | 3-OH, 4-OH | H | H | $CH_3$ | | | |
| Dopamine | 3-OH, 4-OH | H | H | H | P | | |
| Dobutamine | 3-OH, 4-OH | H | H | 1* | | C | |
| Nordefrin | 3-OH, 4-OH | OH | $CH_3$ | H | V | | |
| Ethylnorepinephrine | 3-OH, 4-OH | OH | $CH_2CH_3$ | H | | B | |
| Isoproterenol | 3-OH, 4-OH | OH | H | $CH(CH_3)_2$ | | B, C | |
| Protokylol | 3-OH, 4-OH | OH | H | 2* | | B | |
| Isoetharine | 3-OH, 4-OH | OH | $CH_2CH_3$ | $CH(CH_3)_2$ | | B | |
| Metaproterenol | 3-OH, 5-OH | OH | H | $CH(CH_3)_2$ | | B | |
| Terbutaline | 3-OH, 5-OH | OH | H | $C(CH_3)_3$ | | B | |
| Metaraminol | 3-OH | OH | $CH_3$ | H | P | | |
| Phenylephrine | 3-OH | OH | H | $CH_3$ | N, P | | |
| Tyramine | 4-OH | H | H | H | | | |
| Hydroxyamphetamine | 4-OH | H | $CH_3$ | H | N, P | C | |
| Methoxyphenamine | 2-$OCH_3$ | H | $CH_3$ | $CH_3$ | | B | |

TABLE I-continued

| | | | | | | |
|---|---|---|---|---|---|---|
| Methoxamine | 2-OCH₃, 5-OCH₃ | OH | CH₃ | H | P | |
| Albuterol | 3-CH₂OH, 4-OH | OH | H | C(CH₃)₃ | | B |
| Amphetamine | | H | CH₃ | H | | CNS, 0 |
| Methamphetamine | | H | CH₃ | CH₃ | P | CNS, 0 |
| Benzphetamine | | H | CH₃ | —NHR$^\gamma$ is replaced with 3* | | 0 |
| Ephedrine | | OH | CH₃ | CH₃ | N, P | B, C |
| Phenylpropanolamine | | OH | CH₃ | H | N | |
| Mephentermine | | H | —CHR$^\beta$— is replaced with 4* | CH₃ | N, P | |
| Phentermine | | H | —CHR$^\beta$— is replaced with 4* | H | | 0 |
| Chlorphentermine | 4-Cl | H | —CHR$^\beta$— is replaced with 4* | H | | 0 |
| Fenfluramine | 3-CF₃ | H | CH₃ | C₂H₅ | | 0 |
| Propylhexedrine | 5*: phenyl ring is replaced with cyclohexyl | H | CH₃ | CH₃ | N | |
| Diethylpropion | | 6*: The substituent at the 1-position is replaced with 6, below. | | | | 0 |
| Phenmetrazine | | 7*: The substituent at the 1-position is replaced with 7, below. | | | | 0 |
| Phendimetrazine | | 8*: The substituent at the 1-position is replaced with 8, below. | | | | 0 |

*1:

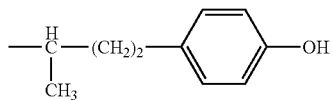

*2:

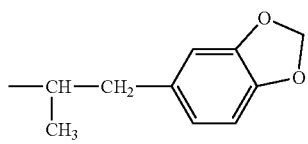

*3:

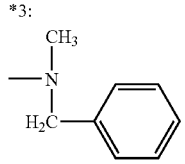

*4:

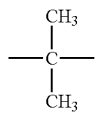

*5:

*6:

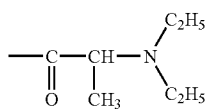

*7:

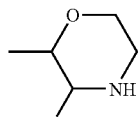

*8:

TABLE I-continued

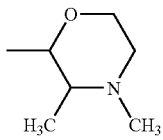

α Activity
A = Allergic reactions (includes β action)
N = Nasal decongestion
P = Pressor (may include β action)
V = Other local vasoconstriction
(e.g. in local anesthesia)

β Activity
B = Bronchodilator
C = Cardiac

CNS = Central nervous system
0 = Anorectic

*Numbers bearing an asterisk refer to the substituents numbered in the bottom rows of the table; substituent 5 replaces the phenyl rings, and 6, 7 and 8 are attached directly to the phenyl ring, replacing the ethylamine side chain.
†The α and β in the prototype formula refer to positions of the C atoms in the ethylamine side chain.

In preferred embodiments, the sympathomimetic agent has anorexient properties (e.g., suppresses appetite) or is anorectic without significant toxicity to a subject or patient (e.g., a human) at therapeutically effective doses. In a more preferred embodiment, the sympathomimetic agent has anorexient properties (e.g., suppresses appetite) or is anorectic without loss of efficacy or without adverse or undesirable side effects to a subject or patient (e.g., a human subject or patient) at therapeutically effective doses when prescribed in combination with topiramate. In yet another embodiment, the sympathomimetic agent is phentermine or a phentermine-like compound. As defined herein, a phentermine-like compound is a compound structurally related to phentermine (e.g., an analog or derivative) which maintains an anorectic activity similar to that of phentermine. A preferred phentermine-like compound is chlorphentermine. In yet another embodiment, the sympathomimetic agent is amphetamine or an amphetamine-like compound. As used herein, an amphetamine-like compound is a compound structurally related to amphetamine (e.g., an analog or derivative) which maintains an anorectic effect of amphetamine. In yet another embodiment, the sympathomimetic agent is phenmetrazine or a phenmetrazine-like compound. As defined herein, a "phenmetrazine-like compound" is a compound structurally related to phenmetrazine (e.g., an analog or derivative) which maintains an anorectic effect of phenmetrazine. A preferred phenmetrazine-like compound is phendimetrazine. Analogs and/or derivatives of the compounds of the present invention can be tested for their ability to suppress appetite (e.g., suppress food intake) in a subject (e.g., a mammalian subject).

In an exemplary preferred embodiment, the sympathonimetic agent is selected from the group consisting of amphetamine, methamphetamine, benzphetamine, phenylpropanolamine, phentermine, chlorphentermine, diethylpropion, phenmetrazine, and phendimetrazine (as set forth in Table I. In a particularly preferred embodiment, the sympathomimetic agent is phentermine. It is also within the scope of the present invention to utilize other sympathomimetic agents including pseudo ephedrine (a stereoisomer of ephedrine, SUDAFED®), methylphenidate (RITALIN®), tuaminoheptane, and other CNS stimulants including, for example, caffeine.

The terms "anticonvulsant sulfamate derivative" and "anticonvulsant sulfamate derivatives" are terms of art and refer to a class of sulfamate-derived compounds that possess anticonvulsant activity and have an art-recognized use in the treatment of epilepsy. In particular, the anticonvulsant sulfamate derivatives are monosaccharide derivatives with sulfamate functionality. The anticonvulsant sulfamate derivatives for use in the present invention have one or more of the following modes of activity: modulation of voltage-dependent sodium conductance; potentiation of gamma-aminobutyric acid-evoked currents; inhibition of the kainate/alpha-amino-3-hydroxy-5-methylisoxazole-4-propionic acid (AMPA) subtype of the glutamate receptor; and/or inhibition of carbonic anhydrase (e.g, a mechanism by which the anticonvulsant derivative of the present invention may decrease the sensation of taste). The anticonvulsant sulfamate derivatives for use in the present invention are described further in U.S. Pat. Nos. 4,513,006, 5,384,327, 5,498,629, 5,753,693 and 5,753,694, as are methods of synthesizing such anticonvulsant sulfamate derivatives. The aforementioned patents are incorporated by reference herein in their entireties.

In preferred embodiments, the anticonvulsant sulfamate derivative is a compound having the following formula (I):

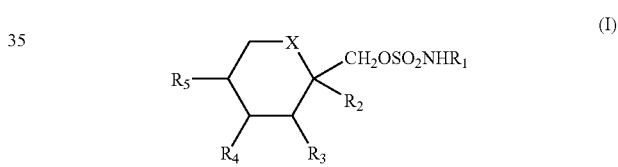

(I)

wherein:
X is $CH_2$ or O;
$R_1$ is H or alkyl; and
$R_2$, $R_3$, $R_4$ and $R_5$ are independently H or lower alkyl, with the proviso that when X is O, then $R_2$ and $R_3$ and/or $R_4$ and $R_5$ together may be a methylenedioxy group of the following formula (II):

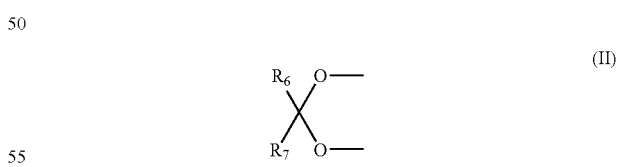

(II)

in which $R_6$ and $R_7$ are the same or different and are H or lower alkyl, or are joined to form a cyclopentyl or cyclohexyl ring.

$R_1$ in particular is hydrogen or alkyl of about 1 to 4 carbons, such as methyl, ethyl, or isopropyl. Alkyl includes both straight and branched chain alkyl. Alkyl groups $R_2$, $R_3$, $R_4$, $R_5$, $R_6$ and $R_7$ are about 1 to 3 carbons and include methyl, ethyl, isopropyl and n-propyl.

A particular group of compounds of the formula (I) are those wherein X is oxygen and both $R_2$ and $R_3$, and $R_4$ and $R_5$ together are methylenedioxy groups of the formula (II), wherein $R_6$ and $R_7$ are both hydrogen, both alkyl, or combine to form a spiro cyclopentyl or cyclohexyl ring, in particular, where $R_6$ and $R_7$ are both alkyl such as methyl. A second group of compounds are those wherein X is $CH_2$ and $R_4$ and $R_5$ are joined to form a benzene ring. A third group of compounds of the formula (I) are those wherein both $R_2$ and $R_3$ are hydrogen.

In preferred embodiments, the anticonvulsant sulfamate derivatives have anorexient properties (e.g., suppress appetite) without significant toxicity to a subject or patient (e.g., a human) at therapeutically effective doses. In a more preferred embodiment, the anticonvulsant sulfamate derivatives have anorexient properties (e.g., suppress appetite) without significant adverse or undesirable side effects to a subject or patient (e.g., a human) at therapeutically effective doses when prescribed in combination with phentermine. In a particularly preferred embodiment the anticonvulsant sulfamate derivative is topiramate (Topamax®). Topiramate, also referred to in the art as 2,3:4,5-bis-O-(1-methylethylidene)-β-D-fructo-pyranose sulfamate, has been demonstrated in clinical trials of human epilepsy to be effective as an adjunctive therapy or as monotherapy in treating simple and complex partial seizures and secondarily generalized seizures (E. Faught et al. (1995) *Epilepsia* 36(suppl 4):33; S. Sachdeo et al. (1995) *Epilepsia* 36(suppl 4):33) and is currently marketed for the treatment of simple and complex partial seizure epilepsy with or without secondary generalized seizures.

Dosages, Administration and Pharmaceutical Compositions:

The choice of appropriate dosages for the drugs used in combination therapy according to the present invention can be determined and optimized by the skilled artisan, e.g., by observation of the patient, including the patient's overall health, the response to the combination therapy, and the like. Optimization, for example, may be necessary if it is determined that a patient is not exhibiting the desired therapeutic effect or conversely, if the patient is experiencing undesirable or adverse side effects that are too many in number or are of a troublesome severity.

Preferably, a sympathomimetic drug (e.g., a drug set forth in Table I) is prescribed at a dosage routinely used by the skilled artisan (e.g., physician) to promote the desired therapeutic effect of the drug, when the drug is used as a monotherapy. Preferably, an anticonvulsant sulfamate derivative (e.g., a compound having formula I) is prescribed at a lower dosage than routinely used by the skilled artisan (e.g., physician) to promote the desired therapeutic effect of the drug, when the drug is used as a monotherapy (e.g., in the treatment of epilepsy). In a preferred embodiment, a sympathomimetic drug or anticonvulsant sulfamate derivative is prescribed at a dose of between 5-1000, preferably between 10-1500, more preferably between 20-1000 and most preferably between 25-50 mg daily.

It is especially advantageous to formulate compositions of the invention in unit dosage form for ease of administration and uniformity of dosage. The term "unit dosage forms" as used herein refers to physically discrete units suited as unitary dosages for the individuals to be treated. That is, the compositions are formulated into discrete dosage units each containing a predetermined, "unit dosage" of an active compound calculated to produce the desired therapeutic effect in association with the required pharmaceutical carrier. The specifications of the novel dosage unit forms of the invention are dependent on the unique characteristics of the composition containing the anticonvulsant or sympathomimetic agent and the particular therapeutic effect to be achieved. Dosages can further be determined by reference to the usual dose and manner of administration of the ingredients. It is also within the scope of the present invention to formulate a single physically discrete dosage form having each of the active ingredients of the combination treatment (e.g., a single dosage form having an anticonvulsant agent and a sympathomimetic agent).

The method of administration of compositions or combinations of the invention will depend, in particular, on the type of sympathomimetic agent used and the chosen anticonvulsant sulfamate derivative. The sympathomimetic agent and the anticonvulsant sulfamate derivative may be administered together in the same composition or simultaneously or sequentially in two separate compositions. Also, one or more sympathomimetic agents or one or more anticonvulsant sulfamate derivatives may be administered to a subject or patient either in the form of a therapeutic composition or in combination, e.g., in the form of one or more separate compositions administered simultaneously or sequentially. The schedule of administration will be dependent on the type of sympathomimetic agent(s) and anticonvulsant sulfamate derivative(s) chosen. For example, a sympathomimetic agent can have a stimulant effect and the degree of such stimulant effect may vary depending on the sympathomimetic agent chosen. Accordingly, a sympathomimetic agent having a significant stimulant effect might be administered earlier in the day than administration of a sympathomimetic agent having a lesser stimulant effect. Likewise, an anticonvulsant sulfamate derivative can have a sedative effect and the degree of such sedative effect may vary depending on the anticonvulsant sulfamate derivative chosen. Accordingly, an anticonvulsant sulfamate derivative having a significant sedative effect might be administered later in the day than administration of an anticonvulsant sulfamate derivative having a lesser sedative effect. Moreover, sympathomimetic agents and/or anticonvulsant agents having lesser stimulant or sedative effects, respectively, may be administered simultaneously.

Sympathomimetic agents and/or anticonvulsant sulfamate derivatives can also be administered along with a pharmaceutically acceptable carrier. As used herein "pharmaceutically acceptable carrier" includes any solvents, dispersion media, coatings, antibacterial and antifungal agents, isotonic and absorption delaying agents, and the like. The use of such media and agents for pharmaceutically active substances is well known in the art. Except insofar as any conventional media or agent is incompatible with the active compound, use thereof in compositions of the invention is contemplated.

A sympathomimetic agent alone, or in combination with an anticonvulsant sulfamate derivative in the form of a composition, is preferably administered orally. When the composition(s) are orally administered, an inert diluent or an assimilable edible carrier may be included. The composition and other ingredients may also be enclosed in a hard or soft shell gelatin capsule, compressed into tablets, or incorporated directly into the individual's diet. For oral therapeutic administration, the composition may be incorporated with excipients and used in the form of ingestible tablets, buccal tablets, troches, capsules, elixirs, suspensions, syrups, wafers, and the like. The percentage of the compositions and preparations may, of course, be varied. The amount of active compound in such therapeutically useful compositions is such that a suitable dosage will be obtained. In a particularly preferred embodiment, the present invention includes pharmaceutical composition comprising a therapeutically effective amount of a sympathomimetic agent and an anticonvulsant sulfamate derivative. In one embodiment, the present invention includes a therapeutically-effective amount of a sympathomimetic agent and an anticonvulsant sulfamate derivative packaged in a daily dosing regimen (e.g., packaged on cards, packaged with dosing cards, packaged on blisters or blow-molded plastics, etc.). Such packaging promotes products and increases patient compliance with drug regimens. Such packaging can also reduce patient confusion. The present invention also features such kits further containing instructions for use.

The tablets, troches, pills, capsules and the like may also contain a binder, an excipient, a lubricant, or a sweetening agent. Various other materials may be present as coatings or to otherwise modify the physical form of the dosage unit. For instance, tablets, pills, or capsules may be coated with shellac, sugar or both. Of course, any material used in preparing any dosage unit form should be pharmaceutically pure and substantially non-toxic in the amounts employed.

A sympathomimetic agent, alone or in combination with an anticonvulsant sulfamate derivative, can also be administered in a convenient manner such as by injection (subcutaneous, intravenous, etc.), inhalation, transdermal application, or rectal administration. Depending on the route of administration, the composition containing the sympathomimetic agent and/or anticonvulsant sulfamate derivative may be coated with a material to protect the compound from the action of acids and other natural conditions which may inactivate the compounds or compositions.

To administer the compositions, for example, transdermally or by injection, it may be necessary to coat the composition with, or co-administer the composition with, a material to prevent its inactivation. For example, the composition may be administered to an individual in an appropriate diluent or in an appropriate carrier such as liposomes. Pharmaceutically acceptable diluents include saline and aqueous buffer solutions. Liposomes include water-in-oil-in-water CGF emulsions as well as conventional liposomes (Strejan et al. (1984) *J. Neuroimmunol.* 7:27). To administer the compositions containing the sympathomimetic agents and/or anticonvulsant sulfamate derivatives parenterally or intraperitoneally, dispersions can be prepared in glycerol, liquid polyethylene glycols, and mixtures thereof and in oils. Under ordinary conditions of storage and use, these preparations may contain a preservative to prevent the growth of microorganisms.

Compositions suitable for injectable use include sterile aqueous solutions (where water soluble) or dispersions and sterile powders for the extemporaneous preparation of sterile injectable solutions or dispersion. In all cases, the composition must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene gloycol, and the like), suitable mixtures thereof, and vegetable oils. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents. In many cases, it will be preferable to include isotonic agents, for example, sugars, polyalcohols such as mannitol and sorbitol, or sodium chloride in the composition. Prolonged absorption of the injectable compositions can be brought about by including in the composition an agent which delays absorption, for example, aluminum monostearate and gelatin.

A preferred aspect of the present invention features prescribing phentermine in combination with topiramate to effect weight loss and/or to treat Syndrome X and/or a subset of symptoms thereof. A preferred dose for phentermine is between about 5-60 mg daily, including but not limited to doses of 8, 10, 15, 20, 25, 30, 35, 40, 45, 50 and 55 mg daily. A particularly preferred dose for phentermine is about 15 mg daily. In an exemplary embodiment, the phentermine is of an immediate release form.

Preferably, the phentermine is taken by the patent in the morning and more preferably, is taken before breakfast. The phentermine is best taken in the morning because the drug is a stimulant as well as an appetite suppressant. When phentermine is prescribed (e.g., as part of the combination therapy described herein), physicians should be aware and may want to advise patients that the drug can be mildly habit forming. Phentermine can also cause increased nervousness, increased energy, irritability and, rarely, insomnia. Stopping phentermine may also cause tiredness lasting for up to 1-2 weeks. Phentermine can also raise blood pressure (e.g., during the early phases of treatment).

A preferred dose for topiramate is between about 50-1500 mg daily. As discussed previously, prescription of topiramate at dosages of ≧400 mg daily results is promotion of undesirable side effects (e.g., sedation, mental clouding). Accordingly, in a preferred embodiment, topiramate is prescribed at a dose of about 50-400 mg daily. In another preferred embodiment, the dosage of topiramate is increased gradually at the outset of the therapy in order to reduce the chance of undesirable side effects associated with higher doses of the drug. In an exemplary embodiment, the topiramate is administered at a dose of 25 mg daily for about the first 5-7 days (e.g., 6 days) of treatment, at a dose of about 50 mg daily for the next 5-7 days (e.g., 6 days), at a dose of 100 mg daily for about the next 6-8 days (e.g., 7 days) and about 150 mg daily for the next 20-26 days. From this point forward, the topiramate can be administered at a dose of 150-250 mg daily, including but not limited to doses of 175, 200, and 225 mg daily. A particularly preferred dose for continued therapy is about 200 mg of topiramate daily. In another exemplary embodiment, the topiramate is of an immediate release form. In yet another exemplary embodiment, the topiramate is of a sustained release form.

In a preferred embodiment, topiramate is taken later in the day than the phentermine. Preferably, the patient takes the topiramate just before supper or later in the evening. Topiramate is best given later in the day because the drug can be sedating. In other embodiments, the topiramate is given BID (e.g., twice daily), TID (three times daily) or QID (four time daily). When prescribing topiramate, physicians should be aware and may want to advise patients that the drug can cause tiredness, fatigue, dizziness, difficulty with speech or finding words, difficulty concentrating, difficulty with balance, and/or numbness or tingling in the hands or feet. Less common side effects are nausea, coordination problems, abdominal pain, slowed thinking nervousness, depression, breast pain, painful periods, double or blurred vision, palpitations, low white blood count and kidney stones. A physician should also advise patients that the drug may not be taken if the patient is also taking Diamox (acetazolamide). No female patient should become pregnant while taking this drug as it may cause birth defects. If a female patient misses a period she should immediately discontinue taking the medication and inform the physician. Female patients should not be treated according to the methods of the present invention if breast feeding a child. Patients should not drink alcohol or take sedating medications while taking topiramate since excess sedation can occur. Patients should also refrain from performing dangerous tasks (e.g. operating heavy machinery or driving) until they are comfortable with the side effects of the full dose (e.g., 200-400 mg daily). Patients should be advised not to increase the dosage beyond what is prescribed. Topiramate is not habit forming.

Yet another embodiment of the present invention features pharmaceutical compositions (e.g., for oral administration) comprising phentermine and topiramate in a single pharmaceutical formulation. Such compositions may be preferred, for example, to increase patient compliance (e.g., by reducing the number of administrations necessary to achieve the desired pharmacologic effect).

In a preferred embodiment, the pharmaceutical composition includes phentermine in an immediate release form and further includes topiramate in a controlled release formulation. As defined herein, an "immediate release formulation" is one which has been formulated to allow, for example, the phentermine, to act as quickly as possible. Preferred immediate release formulations include, but are not limited to, readily dissolvable formulations. As defined herein, a "controlled release formulation" includes a pharmaceutical formulation that has been adapted such that drug release rates and drug release profiles can be matched to physiological and chronotherapeutic requirements or, alternatively, has been formulated to effect release of a drug at a programmed rate. Preferred controlled release formulations include, but are not limited to, granules, delayed release granules, hydrogels (e.g., of synthetic or natural origin), other gelling agents (e.g., gel-forming dietary fibers), matrix-based formulations (e.g., formulations comprising a polymeric material having at least one active ingredient dispersed therethrough), granules within a matrix, polymeric mixtures, granular masses, and the like.

In one embodiment, a controlled release formulation is a delayed release form. As defined herein, a "delayed release form" is formulated in such a way as to delay, for example, topiramate's action for an extended period of time. A delayed release form can be formulated in such a way as to delay the release of an effective dose of topiramate for 4, 8, 12, 16 or 24 hours following the release of phentermine. In yet another preferred embodiment, a controlled release formulation is a sustained release form. As defined herein, a "sustained release form" is formulated in such a way as to sustain, for example, the topiramate's action over an extended period of time. A sustained release form can be formulated in such a way as to provide an effective dose of topiramate (e.g., provide a physiologically effective blood level) over a 4, 8, 12, 16 or 24 hour period.

Preferred compositions include a tablet core consisting essentially of topiramate, said core being in association with a layer of phentermine. Preferably, the core has a delayed or sustained dissolution rate. In an exemplary embodiment, a tablet can comprise a first layer containing, for example, phentermine (e.g., in an immediate release formulation) and a core containing, for example, topiramate in a delayed release or sustained release formulation. Other exemplary embodiments can include, for example, a barrier between the first layer and core, said layer serving the purpose of limiting drug release from the surface of the core. Preferred barriers prevent dissolution of the core when the pharmaceutical formulation is first exposed to gastric fluid. For example, a barrier can comprise a disintegrant, a dissolution-retarding coating (e.g., a polymeric material, for example, an enteric polymer), or a hydrophobic coating or film, and can be selectively soluble in either the stomach or intestinal fluids. Such barriers permit the topiramate to leach out slowly and can cover substantially the whole surface of the core.

The above-described pharmaceutical compositions are designed to release the two effective agents of the combination therapy of the present invention sequentially, i.e., releasing topiramate after releasing phentermine, both agents being contained in the same pharmaceutical composition. Preferred amounts of phentermine and topiramate are as described above with particularly preferred compositions comprising from about 5 mg to about 60 mg phentermine and from about 50 mg to 1500 mg topiramate. Particularly preferred compositions include at least 15 mg phentermine and at least about 50 mg, 100 mg or 200 mg topiramate.

Pharmaceutical compositions so formulated may contain additional additives, suspending agents, diluents, binders or adjuvants, disintegrants, lubricants, glidants, stabilizers, coloring agents, flavors, etc. These are conventional materials which may be incorporated in conventional amounts.

In one embodiment, a method of the present invention is carried out, practiced or performed such that weight loss in the subject or patient occurs. Accordingly, the methods of the present invention are particularly useful for the treatment of overweight or obese patients. As defined herein, "overweight" subjects or patients are between about 1 and 20 percent overweight (e.g., weighs 1-20% in excess of their ideal body weight). Also as defined herein, an "obese" subject or patient is greater than 20 percent overweight (e.g., weighs >20% in excess of his or her ideal body weight). Alternatively, the methods of the present invention are useful in the treatment of subjects or patients in need of losing weight, but who are not necessarily overweight or obese. For example, it may be desirable to achieve weight loss in subjects or patients having arthritis or prostheses such that the individual experiences less adverse effects resulting from bearing weight.

The combination therapies of the present invention will generally be administered until the patient has experienced the desired weight loss, and preferably has achieved an ideal body weight. Alternatively, the combination therapies of the present invention can be administered until the patient has achieved a weight loss of 5-10%, 10-15%, 15-20% or 20-25% of their initial body mass (e.g., the patient's starting weight).

The present inventor has also recognized that the combination therapy of the present invention ameliorates symptoms associated with Syndrome X. Syndrome X consists of a complex of medical problems that are largely associated with obesity, including, hypertension, diabetes or glucose intolerance and insulin resistance, hyperlipidemia, and often tiredness and sleepiness associated with sleep apnea. Patients are often treated with combinations of antihypertensives, lipid lowering agents, insulin or oral diabetic drugs, and various mechanical and surgical treatments of sleep apnea. However, such treatments are often costly and do not treat the underlying problem of obesity. Moreover, some of the treatments for diabetes, including insulin and oral diabetic agents, actually aggravate Syndrome X by increasing insulin levels, increasing appetite, and increasing weight. This can lead to higher blood pressure and even higher cholesterol. Accordingly, one aspect of the present invention features a method of treating Syndrome X using the combination therapies described herein. In one embodiment, the invention features a method of treating Syndrome X in a subject or patient which includes treating the subject with a therapeutically effective amount of a combination of an anticonvulsant sulfamate derivative (e.g., topiramate) and a sympathomimetic agent (e.g., phentermine or a phentermine-like compound), such that at least one symptom associated with Syndrome X is affected. As defined herein, "affecting a symptom" (e.g., affecting a symptom associated with Syndrome X) refers to lessening, decreasing the severity of the symptom or reversing, ameliorating, or improving the symptom (e.g., decreasing hypertension, ameliorating diabetes, reversing glucose intolerance or insulin resistance, lessening hyperlipidemia, or decreasing tiredness and sleepiness associated with sleep apnea).

Treatment of Syndrome X according to the methods of the present invention includes affecting at least one, preferably two, more preferably three, more preferably four, five or six symptoms associated with Syndrome X. In a particularly preferred embodiment, all symptoms associated with Syndrome X are affected (e.g., lessened, reversed, ameliorated, etc.).

The present inventor has also recognized that the combination therapy of the present invention ameliorates some side effects associated with obesity, as described herein. Accordingly, one aspect of the present invention features a method of treating at least one side effect associated with obesity using the combination therapies described herein. In one embodiment, the invention features a method of treating at least one obesity-related side effect in a subject or patient which includes treating the subject with a therapeutically effective amount of a combination of an anticonvulsant sulfamate derivative (e.g., topiramate) and a sympathomimetic agent (e.g., phentermine or a phentermine-like compound), such that at least one obesity-related side effect is effected. As defined herein, a "side effect associated with obesity" includes a symptom or disorder in a subject (e.g., a patient) which is secondary and/or results from (e.g., directly and/or indirectly results from) a medical condition for which the subject is obese and/or being treated. In a preferred embodiment, the subject is obese and/or is being treated for obesity. In another embodiment, the subject has at least one or more (e.g., two, three, four, five or more) side effect(s) selected from the group consisting of sleep apnea, high blood pressure and high blood sugar, high blood lipid, high Hgb A1C or other art-recognized side effects associated with obesity.

Whether in the treatment of Syndrome X or in the practicing of the methods of the present invention to effect weight loss (e.g., in the treatment of overweight and/or obesity) or in treatment of side effects associated with obesity, it will be apparent to the skilled artisan (e.g., physician) that monitoring of the patient is needed to determine the effectiveness of the treatments and to potentially modify the treatments (e.g., modify the dosing, time of drug administration, sequence of drug administration, as defined herein). Accordingly, in certain embodiments, the patient is monitored about every 2-6, preferably every 3-5 and more preferably every 4 weeks. Monitoring the effective of treatment to achieve weight loss includes, but is not limited to monitoring the subject or patient's body weight (e.g., comparing the patient's initial body weight to that at a follow-up visit, for example, four weeks after the initiation of treatment). Additional features of the subject or patient's health can also be monitored (i.e., monitoring the patient's overall health and/or monitoring the effectiveness of treatment of an undesired side effect of obesity) including, but not limited to the patient's blood pressure, blood sugar, serum lipid levels, etc. Likewise, monitoring a subject or patient for treatment of Syndrome X can include monitoring of at least one, preferably more than one symptom associated with Syndrome X.

This invention is further illustrated by the following examples which should not be construed as limiting. The contents of all references, patents, and published patent applications cited throughout this application are hereby incorporated by reference.

EXAMPLE 1

Patients as part of the following trial were treated according to the following dosage regimen. Patients took phentermine at a dose of 15 mg daily throughout the weight loss program, before breakfast. For the first 6 days, patients took one 25 mg tablet of topiramate before supper. For the next 6 days, patients took two 25 mg tablets of topiramate before supper. For the next 7 days (days 13-19), patients took 100 mg before supper daily using 4-25 mg tablets of topiramate daily. For days 20-26, patients took 150 mg of topiramate daily consisting of one-half of a 200 mg tablet and two 25-mg mg tablets of topiramate. From that point on, unless instructed otherwise by the physician, patients continued to take one 200 mg topiramate tablet daily before supper and continued the 15 mg phentermine daily in the morning. Patients were advised to drink at least eight (8) full glasses of water daily to reduce the risk of kidney stones which may result from taking topiramate.

Patients were advised that while the effect of phentermine is fairly rapid, the effect of topiramate is slower in onset. The weight reduction effect of topiramate will continue for as long as 18 months on the medication. That is, the patient can expect to continue gradual weight loss for up to 18 months on the medication. Of course, weight loss is maximal if the patient follows diet and/or exercise programs. The weight loss should exceed 15% of the patients starting weight. Thus, if the patient weighs about 200 pounds as of the start date, he/she might expect to lose at least 30 pounds in a period of 12-18 months. The following patient data has been collected.

TABLE II

| Patient's Initials | Age | Sex | Start Weight (lbs) | Start Blood Pressure | Follow-Up Date | Follow-Up Weight (lbs) | % Weight Loss | Follow-Up Blood Pressure |
|---|---|---|---|---|---|---|---|---|
| M. O.[1] | 48 | F | 182 | 115/70 | 5 weeks | 177 | 2.7% | 120/80 |
|  |  |  |  |  | 9 weeks | 176 | 3.3% | 110/70 |
| T. M. | 37 | F | 190 | 122/84 | 2 weeks, 5 days | 178 | 6.3% | 110/80 |
|  |  |  |  |  | 6 weeks, 2 days | 168 | 11.6% | 125/80 |
| D. M. (A) | 28 | M | 286 | 138/90 | 4 weeks | 279 | 2.4% | 128/86 |
| P. L. | 55 | F | 144 | 132/84 | 4 weeks | 141 | 2.1% | 138/85 |
|  |  |  |  |  | 9 weeks | 137 | 4.9% | 122/82 |
| E. K. | 52 | F | 181 | 130/100 | 5 weeks | 175 | 3.3% | 140/88 |
| I. F. | 41 | F | 196 | 95/60 | 6 weeks, 5 days |  |  |  |
| D. M. (B)[2] | 56 | M | 295 | 150/80 | 4 weeks, 2 days | 297 | (+0.7%) | 148/82 |
|  |  |  |  |  | 8 weeks, 2 days | 287 | 2.7% | 140/70 |

[1] Patient M. O. was being treated with Meridia ® at the onset of the study, which continued through the first 5 weeks of the study. At the 5-week follow up, M. O. was switched to the phentermine/topiramate regime described above.
[2] Patient D. M. (B) was being treated with phentermine alone at the onset of the study and was taking the full dose of topiramate by the fourth week of the study.

As is apparent from the above-described data, patients not previously treated with an anorexient at the outset of the study experienced an average of about 3.5% weight loss after only 2-6 weeks (e.g., patient T.M. lost 6.3% body weight, patient D.M.(A) lost 2.4% body weight, patient P.L. lost 2.1% body weight and patient E.K. lost 3.3% body weight). After only 6-9 weeks of treatment, patients (not previously treated with an anorexient at the outset of the study experienced an average of about 8.3% weight loss (e.g., patient T.M. lost 11.6% body weight and patient P.L. lost 4.9% body weight). The patient previously on Meridia® (patient M.O.) lost 3.3% body weight after being enrolled in the program for 9 weeks. Moreover, the patient previously on phentermine (patient D.M.(B)) lost a total of 2.7% body weight after being enrolled in the program for about 8 weeks. This particular patient reported that this is the most significant weight loss he has achieved to date, the patient having previously tried other conventional therapies.

In addition to the weight loss reported above, almost all patients enrolled in the study experienced decreased blood pressure. Moreover, patients involved in the study who had previously taken Redux, phen-fen, Meridia and/or other weight loss treatments report that they have not previously experienced the benefits of the combined phentermine/topiramate therapy. Patients report that they have no appetite, can resist food easily, can concentrate and function at work (even in attention-intensive jobs such as computer programming), have more energy and feel better. Patients also report experiencing fewer side effects than any previous weight loss treatments tried.

EXAMPLE 2

Extended results of the trial described in Example 1.

A total of thirteen patients were treated for 1-9 months with phentermine (15 mg daily) in the morning and up to 400 mg of topiramate (median dose 200 mg), in the evening. [Note: Patient D.M.(B) discussed above is not included in this data as he was on phentermine treatment prior to treatment with the combination therapy of the present invention.] Topiramate dose was gradually increased from 25 mg per day in increments of 25-50 mg weekly until either desirable weight loss took place or until side effects limited dose increases. [Note: A fourteenth patient discontinued treatment after 3 days due to nausea.] All thirteen patients tolerated treatment well with minimal side effects. Along with taking medication, patients were instructed to walk at least 30 minutes three times per week and to follow a low fat diet. No patients had taken diet medication for at least 3 months prior to treatment. Average baseline BMI was 32.5 (range 26-48).

Average weight loss for the thirteen patients was 11.8%. For seven patients who were on treatment the longest (range 5-9 months), the average weight loss was 14.4%. Patients reported that they had little or no appetite and that they actually felt better (Topiramate's usefulness is also being investigated as a mood stabilizer) than before therapy. Blood pressure, lipid, glucose, and Hgb A1C values were also favorably affected by this treatment.

Table III sets forth patient data for the thirteen above-described patients treated with the combination therapy of the present invention.

TABLE III

Patient Data: Combination Therapy*

| Patient No. | % of Weight Loss | Baseline BMI | Current BMI | Weeks on Rx | Current Status |
|---|---|---|---|---|---|
| 1 | 7.7 | 38 | 35 | 10 | on Rx |
| 2 | 10.3 | 25 | 23 | 4 | Finished |
| 3 | 6.8 | 48 | 44 | 5 | d/c early - dropped out |
| 4 | 16.8 | 30 | 24 | 35 | on taper |
| 5 | 23.2 | 30 | 23 | 41 | on taper |
| 6 | 8 | 41 | 38 | 40 | on Rx |
| 7 | 9.7 | 28 | 25 | 33 | on taper |
| 8 | 14.4 | 30 | 26 | 44 | on Rx |
| 9 | 15.9 | 27 | 21 | 32 | on taper |
| 10 | 9 | 33 | 31 | 7 | d/c early - will restart |
| 11 | 12.9 | 28 | 24 | 22 | Finished |
| 12 | 7 | 29 | 27 | 5 | on Rx |
| 13 | 12.1 | 34 | 31 | 6 | on Rx |

*data for thirteen patients
Average weight loss = 11.8% (13 patients)
Average weight loss ≧ 22 weeks on Rx = 14.4% (7 patients)
Average baseline BMI = 32.4

Table IV sets forth for the average blood pressure, blood glucose, Hgb A1C and blood lipid value for the thirteen patients.

TABLE IV

|  | BP mm Hg | GLUCOSE mg/dL | HGBA1C %* | CHOL mg/dL | TRIG mg/dL |
|---|---|---|---|---|---|
| Average Pre-Treatment Value | 131.3/85.9 | 107 | 6.48 | 212 | 189 |
| Average On Treatment Value | 122.6/78.4 | 102 | 5.05 | 210 | 172 |

*Numbers include 1 diabetic patient whose oral hypoglycemic was reduced by 50% while on the weight loss treatment.

One of the thirteen patients in the study also had severe sleep apnea with the usual complications of daytime sleepiness and fatigue. His symptoms have disappeared with the weight loss treatment.

Of the six patients (i.e., finished or on taper) who have completed the combination therapy of the present invention, five of the six achieved a body mass index (BMI) of 24 or better. The average pre-treatment or baseline BMI for these six patients was 28. The final average BMI was 23.3. The average weight loss was 17%.

EXAMPLE 3

The 56-year old male patient described previously (D.M. (B)) who was initially taking phentermine alone and had topiramate added to his regimen had a good effect from the combination. He once weighed as much as 395 pounds. When Redux was still on the mark in the United States, he was treated with a combination of diet, exercise, Redux and phentermine. His lowest weight attained was 285 pounds. When Redux was withdrawn from the market, he remained on phentermine but gained weight back to 295-300 pounds. When topiramate was added to his regimen, he managed to lose 25 pounds and is currently at 271 pounds, his lowest weight since he was in his 20s. He, along with most of the patients treated so far, reported that the treatment with topiramate and phentermine had fewer side effects and was more effective than any previous weight loss treatment using medications that he and others had tried. This 56-year old man exhibited lowered blood pressure (approx. 15 mm Hg systolic and 10 mm Hg diastolic).

EXAMPLE 4

Extended results of the trial described in Examples 1 and 2.

The cumulative data from a total of seventeen patients treated with the combination weight loss treatment of the present invention are set forth in Table V.

TABLE V

Patient Data: Combination Therapy*

| PATIENT | % WEIGHT LOSS | BASELINE BMI | CURRENT BMI | WEEKS ON Rx | CURRENT STATUS |
|---|---|---|---|---|---|
| 1 | 7.7 | 38 | 35 | 33 | on Rx |
| 2 | 10.3 | 25 | 23 | 4 | Finished |
| 3 | 6.8 | 48 | 44 | 5 | d/c early - dropped out |
| 4 | 16.8 | 30 | 24 | 58 | on taper |
| 5 | 23.2 | 30 | 23 | 64 | on taper |
| 6 | 17.5 | 41 | 33 | 63 | on Rx |
| 7 | 9.7 | 28 | 25 | 56 | on taper |
| 8 | 18.6 | 30 | 24 | 67 | on Rx |
| 9 | 15.9 | 27 | 21 | 55 | on taper |
| 10 | 9 | 33 | 31 | 7 | d/c early- will restart |
| 11 | 12.9 | 28 | 24 | 22 | Finished |
| 12 | 7 | 29 | 27 | 5 | d/c early- will restart |
| 13 | 12.1 | 34 | 31 | 6 | d/c early- will restart |
| 14 | 22.5 | 46 | 32 | 16 | on Rx |
| 15 | 10.1 | 50 | 45 | 12 | on Rx |
| 16 | 6.4 | 27 | 24 | 4 | Finished |
| 17 | 6.3 | 27 | 25 | 6 | on Rx |

*data for seventeen patients
AVERAGE WEIGHT LOSS = 12.5% (17 patients)
AVERAGE WEIGHT LOSS ≧ 22 WEEKS ON Rx = 15.3% (8 patients)
AVERAGE BASELINE BMI = 33.6

The present invention provides a novel combination therapy for the treatment of obese or overweight patients that can result in weight losses of greater than 5-10%, perhaps even as great as 15-20%. The therapy combines phentermine or a phentermine-like drug with drug previously recognized for the treatment of epileptic seizures, known as topiramate. The combination therapy results in greater initial weight loss than other recognized therapies, potential greater overall weight loss and can be continued for significant periods of time with fewer and less serious side effects than other recognized weight loss treatments. In particular, the combination therapy far surpasses the modeset anorexient effects of phentermine monotherapy and can be continued for significant periods of time without the loss of effectiveness experienced by patients being treated with phentermine alone. Moreover, the combination therapy has been found to ameliorate symptoms associated with Syndrome X and accordingly, has potential use in the treatment of Syndrome X.

Equivalents:

Those skilled in the art will recognize, or be able to ascertain using no more than routine experimentation, many equivalents to the specific embodiments of the invention described herein. Such equivalents are intended to be encompassed by the following claims.

I claim:

1. A method for effecting weight loss in a subject comprising administering to the subject a combination of: (a) a therapeutically effective amount of phentermine, and (b) a therapeutically effective amount of an anticonvulsant sulfamate derivative having the structure of formula I

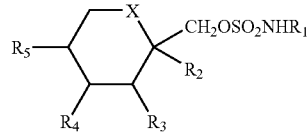

wherein X is $CH_2$ or O, $R_1$, $R_2$, $R_3$, $R_4$, and $R_5$ are independently H or $C_1$-$C_4$ alkyl, and further wherein when X is O, then $R_2$ and $R_3$, and/or $R_4$ and $R_5$, may be taken together to form a methylene dioxy linkage of the formula —O—$CR_6R_7$—O— in which $R_6$ and $R_7$ are independently H or $C_1$-$C_3$ alkyl, or may be taken together to form a cyclopentyl or cyclohexyl ring.

2. The method of claim 1, wherein X is O, $R_1$ is H, $R_2$ and $R_3$ taken together form the methylene dioxy linkage —O—$CH_2$—O—, $R_4$ and $R_5$ taken together form the methylene dioxy linkage —O—$CH_2$—O—, and the anticonvulsant sulfamate derivative is topiramate.

3. The method of claim 2, wherein the therapeutically effective amount of phentermine is from 5 to 60 mg daily.

4. The method of claim 2, wherein the therapeutically effective amount of topiramate is from 50 to 1500 mg daily.

5. The method of claim 4, wherein the therapeutically effective amount of topiramate is less than 400 mg daily.

6. The method of claim 5, wherein the therapeutically effective amount of topiramate is from 50 to 400 mg daily.

7. The method of claim 2, wherein the therapeutically effective amount of phentermine is 15 mg daily.

8. The method of claim 7, wherein the therapeutically effective amount of topiramate is from 50 to 1500 mg daily.

9. The method of claim 8, wherein the therapeutically effective amount of topiramate is less than 400 mg daily.

10. The method of claim 9, wherein the therapeutically effective amount of topiramate is from 50 to 400 mg daily.

11. The method of claim 1, wherein the subject is overweight.

12. The method of claim 1, wherein the subject is obese.

13. The method of claim 1, wherein the subject is neither overweight nor obese.

14. The method of claim 1, wherein the subject suffers from a condition that can be alleviated with loss of body weight.

15. The method of claim 1, wherein the phentermine and the anti-convulsant sulfamate derivative are administered simultaneously.

16. The method of claim 15, wherein the phentermine amine and the anti-convulsant sulfamate derivative are administered in a single pharmaceutical formulation.

17. The method of claim 1, wherein the phentermine and the anti-convulsant sulfamate derivative are administered separately.

18. The method of claim 17, wherein the phentermine and the anti-convulsant sulfamate derivative are administered at different times of day.

19. The method of claim 18, wherein the phentermine is administered in the morning and the anti-convulsant sulfamate derivative is administered at least once later in the day.

20. The method of claim 2, wherein the phentermine and the topiramate are administered simultaneously.

21. The method of claim 20, wherein the phentermine and the topiramate are contained in a single pharmaceutical formulation.

22. The method of claim 2, wherein the phentermine and the topiramate are administered separately.

23. The method of claim 22, wherein the phentermine and the topiramate are administered at different times of the day.

24. The method of claim 23, wherein the phentermine is administered in the morning and the topiramate is administered at least once later in the day.

25. The method of claim 2, wherein the amount of topiramate administered to the subject is gradually increased, over an extended time period, from an initial daily dosage up to a final daily dosage suitable for continued therapy.

26. The method of claim 2, wherein the phentermine is contained in an immediate release dosage form.

27. The method of claim 26, wherein the topiramate is contained in an immediate release dosage form or a controlled release dosage form.

28. The method of claim 2, wherein the phentermine and the topiramate are administered orally.

29. A pharmaceutical composition comprising topiramate and phentermine.

* * * * *

UNITED STATES PATENT AND TRADEMARK OFFICE
CERTIFICATE OF CORRECTION

PATENT NO. : 7,659,256 B2
APPLICATION NO. : 11/385199
DATED : February 9, 2010
INVENTOR(S) : Thomas Najarian It is certified that error appears in the above-identified patent and that said Letters Patent is hereby corrected as shown below:

Column 21, Line 11, Claim 16, "phentermine amine and the anti-convulsant sulfamate derivative are" should read -- phentermine and the anti-convulsant sulfamate derivative are --

Signed and Sealed this

Thirteenth Day of April, 2010

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,659,256 B2 | Page 1 of 1 |
| APPLICATION NO. | : 11/385199 | |
| DATED | : February 9, 2010 | |
| INVENTOR(S) | : Thomas Najarian | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 909 days.

Signed and Sealed this

Fifth Day of October, 2010

David J. Kappos
*Director of the United States Patent and Trademark Office*